United States Patent [19]

Yoshida et al.

[11] 4,430,568

[45] Feb. 7, 1984

[54] CONTAINER INSPECTION SYSTEM

[75] Inventors: Osami Yoshida, Tokyo; Hidekazu Tsuji, Amagasaki; Yoshitada Nomura, Tokyo, all of Japan

[73] Assignee: Mitsubishi Denki Kabushiki Kaisha, Tokyo, Japan

[21] Appl. No.: 303,989

[22] Filed: Sep. 21, 1981

[30] Foreign Application Priority Data

Sep. 22, 1980 [JP] Japan ............................. 55-131854

[51] Int. Cl.³ ......................................... G01N 23/00
[52] U.S. Cl. ............................. 250/358.1; 250/359.1; 378/57
[58] Field of Search ............... 250/358.1, 359.1, 360.1; 378/57, 62

[56] References Cited

U.S. PATENT DOCUMENTS

| | | | |
|---|---|---|---|
| 3,678,278 | 7/1972 | Peil | 378/62 |
| 3,808,444 | 4/1974 | Schneeberger et al. | 378/57 |
| 3,919,467 | 11/1975 | Peugeot | 378/57 |
| 4,216,499 | 8/1980 | Kunze et al. | 378/57 |

Primary Examiner—Janice A. Howell
Attorney, Agent, or Firm—Oblon, Fisher, Spivak, McClelland & Maier

[57] ABSTRACT

A package inspection system is used for automatic inspection of a different content or identification of a content in a package such as a container especially a large container in unloading from a ship without opening or unpacking the container and comprises an X-ray transmitter, an X-ray receiver, and a processing unit for image processing.

3 Claims, 4 Drawing Figures

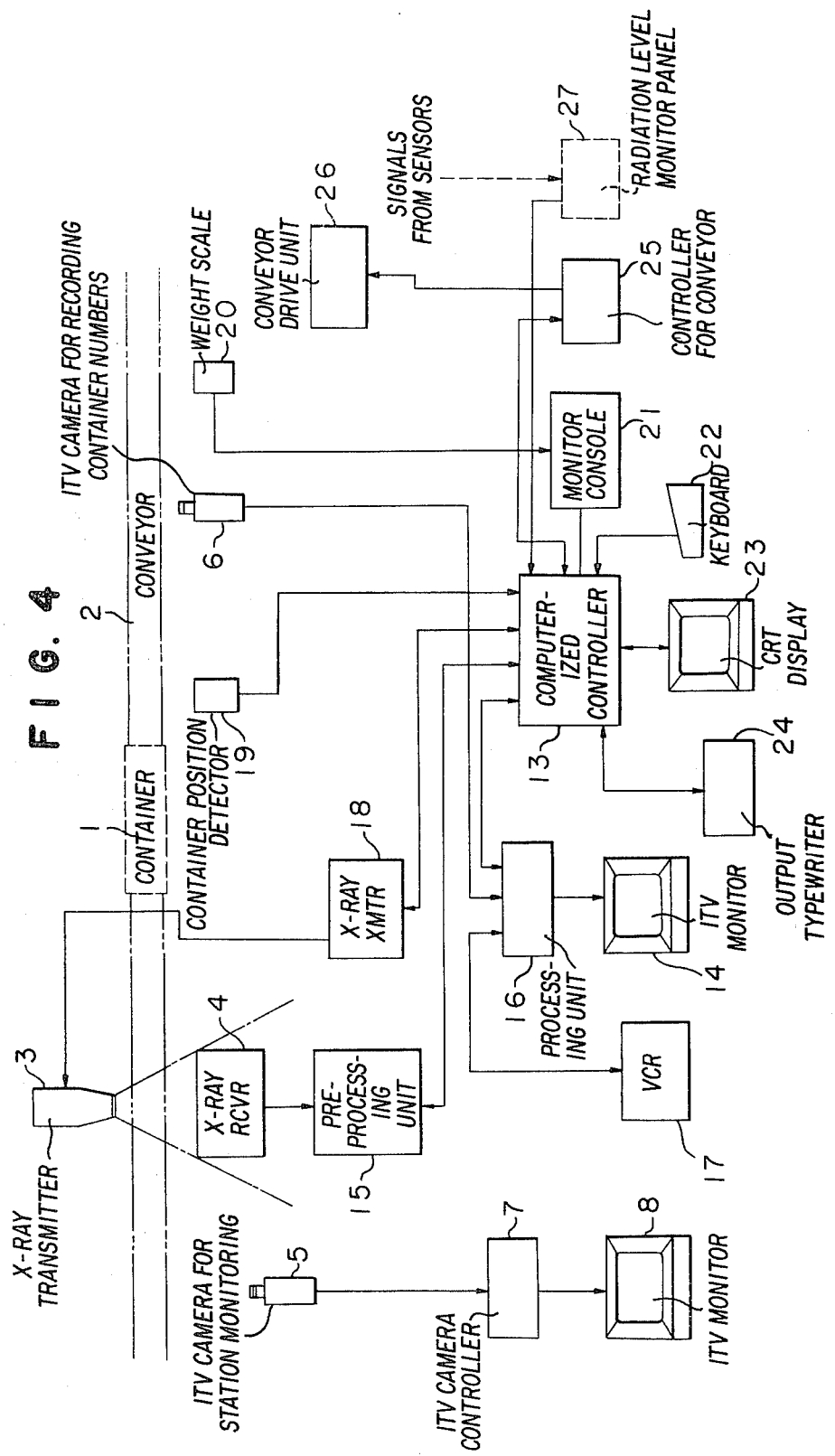

CONTAINER INSPECTION SYSTEM

BACKGROUND OF THE INVENTION

1. Field of the Invention

The present invention relates to a package inspection system for inspection or identification of packages, and particularly containers, in a production or a shipment.

2. Description of the Prior Art

When a product for inspection has large size and is kept in a package such as a container, it is not easily inspected. Thus, an X-ray transmitting system has been employed. When corns are packed in a container and the containers are imported from a foreign country, it is necessary to inspect the containers without opening or unpacking the containers whether a different product such as weapon or alcohol is packed or not or to identify the content in the container to the designated content.

Heretofore, the containers have been irradiated by X-rays and the X-rays transmitted through the container have been displayed on an X-ray fluorescent display device so as to monitor the display device by an operator whether the content in the container is identified to the designated content or a different product is not contained with the operator's experience.

The conventional system will be further illustrated.

An operator operates a conveyor through an operator's console and a controller to shift the container for inspection at a predetermined position for inspection. Then, X-rays are transmitted from an X-ray transmitter by an operator's operation or a signal for detecting reaching of the container at the position for inspection by a controller. Then the X-rays are irradiated to the container. The intensity of the X-rays reached to an X-ray fluorescent display device is modulated depending upon characteristics of the elements of the product in the container to X-rays and the X-rays are converted into visible rays by the display device. As a result, the X-ray transmission pattern of the product in the container is displayed by the display device. When the operator finishes his collection of data for inspection, the container for inspection is shifted to the next step by an operation of the operator's console or an automatic control by the controller.

The operator monitors the pattern displayed on the display device so as to perform his inspection by his experience, whether a different product is contained in the container or not without opening or unpacking the container or changing configuration of the package.

The conventional system has the aforementioned structure. Thus, it is necessary to consider by the operator's experience by using qualitative data as variable density image display and it is not always possible to attain a precise stable consideration.

SUMMARY OF THE INVENTION

In accordance with the present invention, it provides a container inspection system comprising; means for generating an energy flux such as X-rays which transmits inside of the container; sensors for detecting energy level transmitted through the inside of the container; and a processing unit for performing a predetermined image processing under receiving an output signal of the sensor. A signal for variable density of image data for a transmission factor of the container is processed by the processing unit to inspect the container without opening or unpacking the package or changing a configuration of the container.

BRIEF DESCRIPTION OF THE DRAWINGS

FIG. 4 is a block diagram of a detailed structure of the container inspection system of the present invention.

DETAILED DESCRIPTION OF THE PREFERRED EMBODIMENTS

Figure 1:
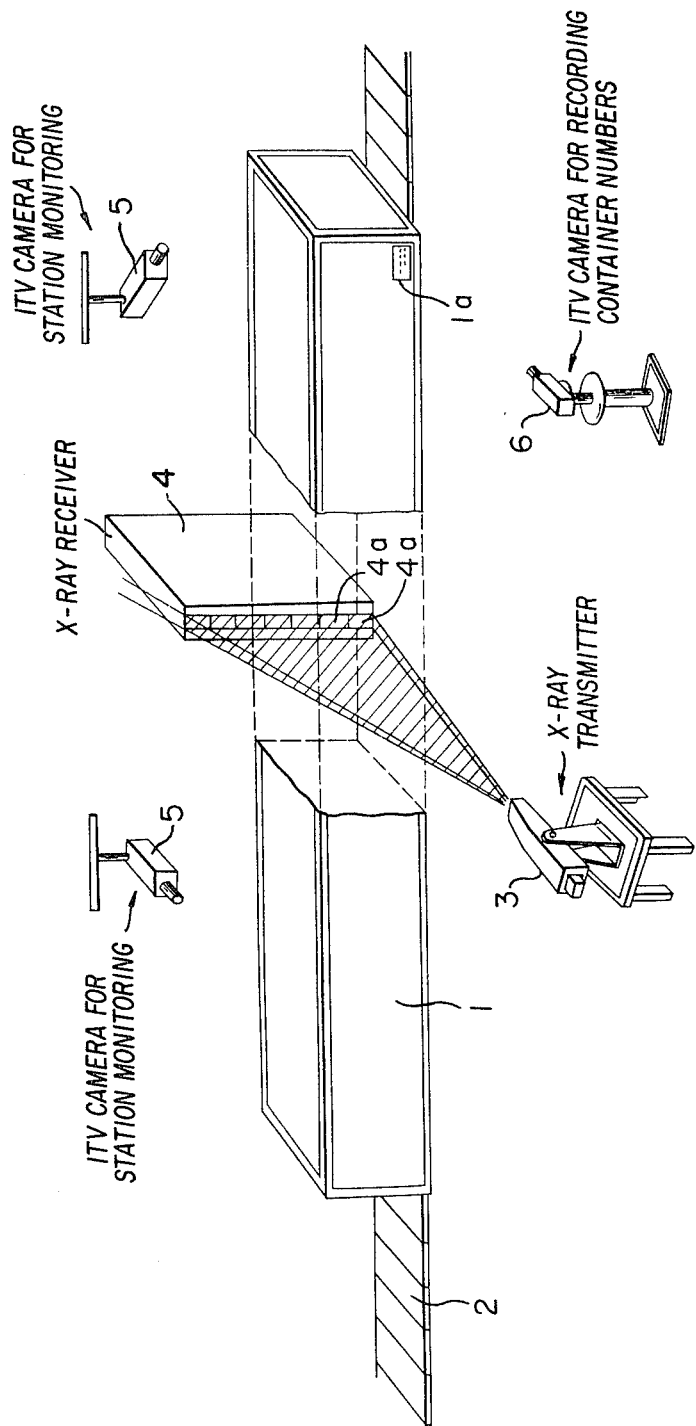
FIG. 1 shows a schematic view of an inspection section of the container inspection system of the present invention.

FIG. 1 shows a container inspection system according to the present invention wherein the reference (1) designates a container (a package for inspection) covered by aluminum or iron plates; (2) designates a conveyor; (3) designates an X-ray transmitter; (4) designates an X-ray receiver having a plurality of X-ray sensors (4a); (5) designates a TV camera for station monitoring; and (6) designates a TV camera for reading container numbers or levels of the container (1).

Figure 3:
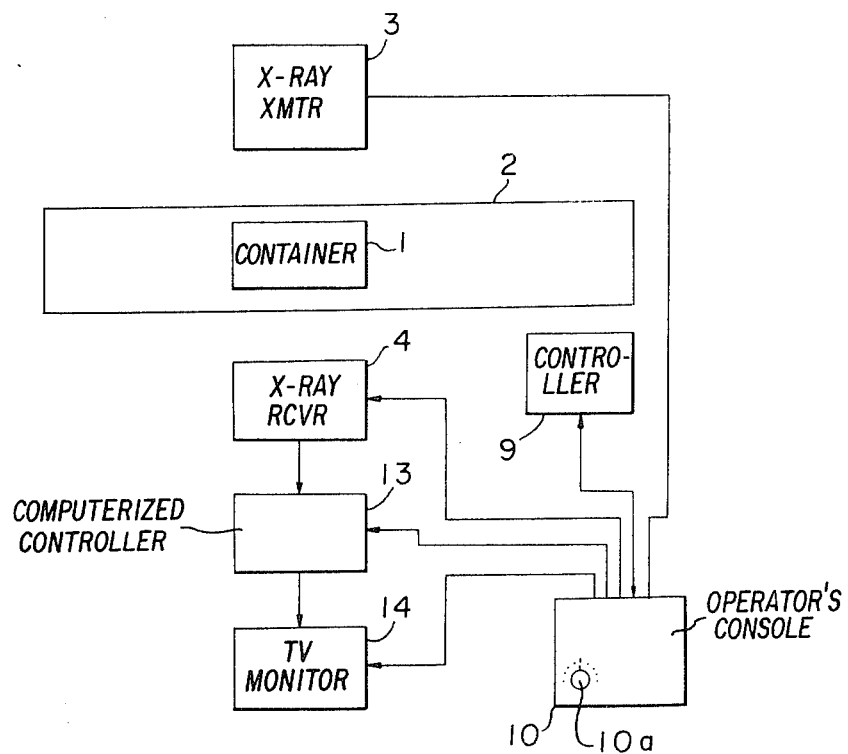
FIG. 3 is a block diagram of one embodiment of the container inspection system of the present invention.

Referring to FIG. 3, the system of the present invention will be illustrated.

In FIG. 3, the references (1), (2), (3) and (4a) designate the same parts described in FIG. 1. The reference (9) designates a control device for the coveyor (2); (10) designates an operator's console; and the container (1) can be transferred to a desired place for inspection through the operator's console (10) and an attenuation level setter (10a) required for image processing is equipped with the operator's console (10) and an inspection processing level can be changed by a control of the setter (10a). The reference (13) designates a computerized controller of a computer; (14) designates a TV monitor for the result of the processing. X-rays are irradiated from the X-ray transmitter (3) to the object container by the operation of the X-ray transmitter (3), the X-ray receiver (4), the computerized controller (13) and the TV monitor (14) through the operator's console (10). The resulting X-rays transmitted through the object container (1) are detected by the X-ray receiver (4) and are processed for a desired image processing by the computerized controller (13) and are displayed on the TV monitor (14).

Figure 2:
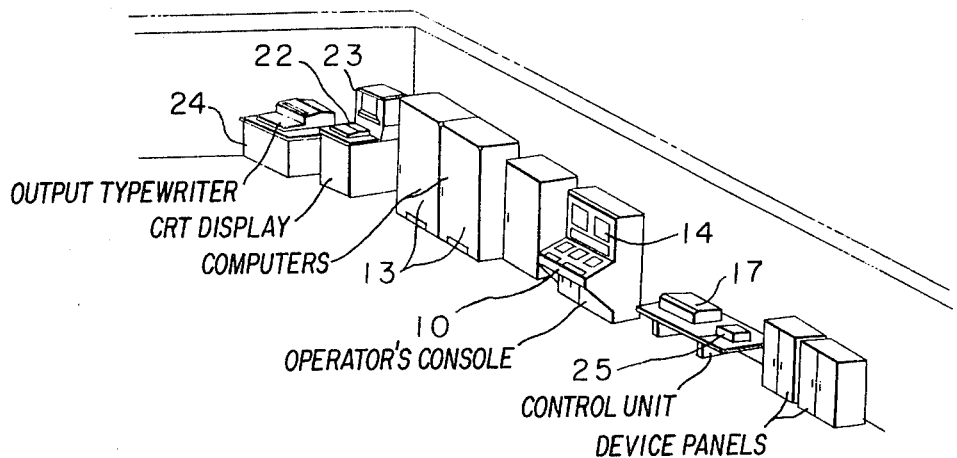
FIG. 2 shows a schematic view of a data processing section of the container inspection system of the present invention.

Referring to FIGS. 2 and 4, the structure of embodiments of the system of the present invention will be further illustrated.

In FIGS. 2 and 4, the references (1) to (6) designate the same parts described in FIG. 1 and reference (7) designates a controller for the TV camera for station monitoring (5). The data received by the TV camera (5) are displayed on a TV monitor (8). The reference (15) designates a pre-processing unit for a primary display processing such as synthesis of the display data or calibration of distortion caused by placements of sensors (4a); (16) designates a processing unit for secondary image processing such as enhancement, binary processing, profile extraction, smoothing, pseudo-color display (color display by converting variable density) of data which are previously processed by the pre-processing unit and an inspected image is displayed on a TV monitor (14). The reference (17) designates a video cassette recorder for recording abnormal images; (18) designates a controller for the X-ray transmitter (3); (19) designates a container position detector; (20) designates a weight scale for measuring a weight of the container (1) in the way passing the container (1) on the conveyor (2) and the measured data are fed to a monitor console (21) connected to the computerized controller (13). A content in the container (1) is identified by the TV camera (6). A predetermined weight is input through a keyboard (22) into the computerized controller (13). The weight measured by the weight scale (20) is compared with the predetermined weight by the monitor console (21) and an abnormal detection is displayed on CRT display (23). The reference (24) designates an output typewriter to print out results of inspections, for example, the results for one day. The reference (25) designates a controller for outputting signal for transferring the container (1) on the conveyor (2) to the conveyor drive unit (26) when it requires certain calibraton of the position of the container by position data of the container position detector (19) or the next container is shifted to the position for the inspection after finishing the inspection of one container (1). The reference (27) designates a radiation level monitor panel for informing excess of X-ray energy over a predetermined level as the abnormal condition.

The operation will be illustrated. An operator operates the converyor (2) through the operator's console (10) and the controller (9) to transfer the container (1) at the predetermined position for the inspection. Then, X-rays are emitted from the X-ray transmitter (3) by the operation through the operator's console (10) or a signal for indicating the arrival of the container (1) to the position for the inspection by the controller (9). When X-rays irradiate the container (1), the intensity of X-rays is modulated depending upon the characteristics for X-rays of the contents of the container (1) and the X-rays are measured by the X-ray receiver (4) and processed for an image processing by the computerized controller (13). As a result, when the attenuation of X-rays over the predetermined value set by the setter (10a) through the operator's console (10) depending upon the content of the container for the inspection, the attenuated value and the configuration and distribution of the region are informed to the operator through the TV monitor (14).

As it is clearly understood by the aforementioned description, the following advantages can be expected by the system of the present invention in comparison with the conventional system.

(1) The labour and experimental skill required for the operator can be reduced.

(2) The fluctuation of the standard for consideration of inspection caused by individual difference and fatigue can be prevented.

(3) The inspection efficiency can be improved.

(4) The data for total consideration are provided to the operator.

In the embodiment, the inspection for detecting a special product in the container by the operator has been illustrated. Thus, it is possible to automatically inspect an abnormal material in various packages by the system for comparing the result of the image processing with an index for an average attenuation of transmitted X-rays; an attenuation at a special position; or a size of a region for the specific attenuation which are previously set in a shipment system or a production line.

In accordance with the present invention, the operation for inspection or identification of a container is attained without opening or unpacking the container or modifying the configuration of the container under preventing the individual difference of the operator the fluctuation of the ability of the operation. Moreover, the inspection quality is improved and the rationalization by the automatic inspection is attained.

In the system of the present invention, the package means in broad meaning and includes any container and any product which internally contains a different part.

We claim:

1. A container inspection system which comprises means for transmitting a container; means for generating an energy flux which is transmitted inside of said container; at least one sensor for detecting an energy level and spatial location of energy flux transmitted through the inside of said container; and a processing unit for performing a predetermined image processing based on an output signal received from said at least one sensor whereby a signal for variable density of image data for a transmission factor of said container is processed by said processing unit to inspect said container without disturbing said container, said processing unit comprising means for storing an index defining a size and a respective predetermined energy flux level, means for comparing said index with the detected energy level and spatial location of said energy flux detected by said at least one sensor; and display means for automatically indicating when said comparing means determines that the energy level and spatial location of the energy flux detected by said at least one sensor matches the stored index.

2. The container inspection system according to claim 1 wherein X-rays are used as the energy flux.

3. The container inspection system according to claim 1 wherein a plurality of sensors for detecting energy level are placed in parallel.

* * * * *